US010729260B2

(12) United States Patent
Suchman et al.

(10) Patent No.: US 10,729,260 B2
(45) Date of Patent: Aug. 4, 2020

(54) WATERPROOF PEEL AWAY TEXTILE PRODUCTS

(71) Applicant: Peel Away Labs, Inc., New York, NY (US)

(72) Inventors: Carol Suchman, New York, NY (US); Maxwell Cohen, New York, NY (US)

(73) Assignee: PEEL AWAY LABS, INC., New York, NY (US)

( * ) Notice: Subject to any disclaimer, the term of this patent is extended or adjusted under 35 U.S.C. 154(b) by 485 days.

(21) Appl. No.: 15/423,050

(22) Filed: Feb. 2, 2017

(65) Prior Publication Data

US 2017/0164766 A1    Jun. 15, 2017

Related U.S. Application Data

(63) Continuation-in-part of application No. 14/036,040, filed on Sep. 25, 2013, now Pat. No. 9,565,955.

(60) Provisional application No. 61/814,558, filed on Apr. 22, 2013, provisional application No. 61/718,816, filed on Oct. 26, 2012.

(51) Int. Cl.
*A47G 9/02* (2006.01)
*A47C 27/00* (2006.01)
*A61F 13/15* (2006.01)
*A47C 31/10* (2006.01)

(52) U.S. Cl.
CPC .......... *A47G 9/0246* (2013.01); *A47C 27/005* (2013.01); *A47C 31/105* (2013.01); *A47G 9/0238* (2013.01); *A61F 13/15203* (2013.01)

(58) Field of Classification Search
CPC .......... A61F 5/485; A61F 13/534; A61F 13/15
See application file for complete search history.

(56) References Cited

U.S. PATENT DOCUMENTS

| | | | | |
|---|---|---|---|---|
| 1,942,287 A | * | 1/1934 | Heitz | A47B 13/086 206/447 |
| 2,262,010 A | * | 11/1941 | Kuehne | A41B 13/10 2/49.2 |
| 2,440,666 A | * | 4/1948 | Witmer | A41B 13/10 2/49.2 |
| 2,763,867 A | * | 9/1956 | Chagnon | A41B 13/10 2/49.1 |
| 3,761,973 A | * | 10/1973 | Leventhal | A61F 5/485 5/484 |
| 4,442,552 A | * | 4/1984 | Bolick | A41B 13/10 2/49.1 |
| 4,903,361 A | * | 2/1990 | Tang | A47G 9/02 5/500 |
| 5,491,844 A | * | 2/1996 | Kehl | A41B 13/10 2/243.1 |
| 5,701,617 A | * | 12/1997 | Colby | A47C 27/006 5/484 |
| 5,991,919 A | * | 11/1999 | Baggetto | A41B 13/10 2/49.1 |

(Continued)

*Primary Examiner* — Peter M. Cuomo
*Assistant Examiner* — Ifeolu A Adeboyejo
(74) *Attorney, Agent, or Firm* — Gottlieb, Rackman & Reisman, P.C.

(57) ABSTRACT

A multi-layered article for bedding or clothing protection formed of a base layer and having a waterproof side, together with a plurality of sheet layers, each sheet layer having a waterproof side; and commonly stitched. The sheet layers are individually removable as needed.

20 Claims, 9 Drawing Sheets

(56) References Cited

U.S. PATENT DOCUMENTS

| | | | | |
|---|---|---|---|---|
| 6,209,156 B1* | 4/2001 | Hershey | ............... | A47G 9/0253 5/487 |
| 6,233,762 B1* | 5/2001 | Bradley | ............... | A47C 21/022 5/484 |
| 6,381,779 B1* | 5/2002 | Thompson | ........... | A47G 9/0223 5/484 |
| 6,493,879 B1* | 12/2002 | Hibler | .................... | A41B 13/10 2/49.1 |
| 7,120,952 B1* | 10/2006 | Bass | .................... | A47C 27/006 5/484 |
| 7,370,380 B2* | 5/2008 | DeFranks | .............. | A47C 27/00 5/483 |
| 2002/0124313 A1* | 9/2002 | Cook | .................. | A47C 27/006 5/484 |
| 2005/0177942 A1* | 8/2005 | Finn | .................... | A47C 27/005 5/499 |
| 2007/0094794 A1* | 5/2007 | Ellis | ....................... | A47G 9/007 5/482 |
| 2009/0119840 A1* | 5/2009 | Seo | ....................... | A01M 29/12 5/487 |
| 2009/0144900 A1* | 6/2009 | Marrache | ............. | A47C 27/005 5/484 |
| 2009/0205134 A1* | 8/2009 | Wootten, Jr. | ......... | A47G 9/0246 5/488 |
| 2010/0154119 A1* | 6/2010 | Shuttleworth | ......... | A47C 21/06 5/484 |
| 2011/0214233 A1* | 9/2011 | Stang | .................. | A47C 21/028 5/488 |

* cited by examiner

WATERPROOF PEEL AWAY TEXTILE PRODUCTS

The present invention is a continuation in part of and claims priority to U.S. patent application Ser. No. 14/036,040, entitled "WATERPROOF PERFORATED LAYERED SHEET", filed on Sep. 25, 2013, presently pending and allowed. This application and U.S. patent application Ser. No. 14/036,040 claim priority to U.S. Provisional Patent Application No. 61/718,816 filed Oct. 26, 2012 and entitled "REMOVABLE LAYERED SHEET" and U.S. Provisional Patent Application 61/814,558 filed Apr. 22, 2013 and entitled, "REMOVABLE LAYERED SHEET." The entire contents of all aforementioned applications are incorporated herein by reference.

BACKGROUND OF THE PRESENT INVENTION

There are over 7.4 million college freshmen and sophomore students in the United States alone. And every year, new students enter the system, so there is a constant influx of students.

College students are known for their 'sloppy' lifestyle and many do not adhere to the cleanliness standards they had at home. This is due to a parent, house cleaner or other person taking care of many of their needs. One of the needs is the changing of sheets that requires the student to take everything off the bed, take off the fitted sheet and take it to the laundry to wash. It can take hours to wash and dry, bring the sheets back to the dorm and remake the bed. Or, the student can send it out which can take a week to get back, so the student needs a second set of bed sheets. Some students end up not washing their sheets all semester.

A dorm (college, high school or ever summer camp) is a hotbed for germs and dirt. Most students not only sleep in their bed, but use it for a workspace, kitchen table, drinking pub, guest lounge and guestroom for romantic encounters and a napping place. Food, dirt and bodily fluids cover the sheets, but they continue to use them without cleaning.

There are other situations and other people where changing sheets can be problematic. For example, babies often soil their sheets and those sheets need to be changed frequently. Changing such a sheet might be problematic if, for example, there isn't a second caregiver at home to hold the baby while the first caregiver changes the sheet.

Similarly, it is common for elderly and/or incontinent people to soil their sheets. In many cases, the elderly person is infirmed or otherwise unable to leave the bed easily. Additionally people recovering from surgical procedures or hospital stays can have wounds that can dirty sheets requiring the sheets to be changed.

As a result, it would be beneficial to have a bedsheet which can more easily and rapidly be replaced than presently occurs. It would be further beneficial for these sheets to be concurrently waterproof or water resistant, so as to protect the underlying mattress and any other materials laid on the mattress. By having a self-waterproof sheet, the speed to replace a sheet improves dramatically.

Similarly, the materials used for an easily replaceable and waterproof bed sheet could be used for pillowcases or blanket covers as well.

It would be beneficial to overcome the problem of excessive time and effort necessary to replace a bedsheet or comparable item, excessive time and effort to clean up possible damage, and to overcome the problem of damaged mattresses thereby shortening the mattress life and incurring unnecessary costs.

SUMMARY OF THE INVENTION

The present invention relates generally to a layered article, such as but not limited to a sheetset, a pillowcase, a blanket cover, a mattress protector, a bib, or an apron; and methods of manufacturing a layered mattress protector. The present invention also relates generally to a layered pillow protector and methods of manufacturing a pillow protector.

The present invention solves the aforementioned problem by providing a multi-layered peel-away article (a "sheetset") that is comprised of a plurality of layered sheets, preferably stitched together with perforations to facilitate easy removal, to reveal a new, fresh, clean layer without having to go through the efforts of cleaning sheets or attaching a new sheet to the bed. That is, a single sheet system may have a plurality of sheets (or pillowcases or blanket covers) stitched together in a way such that when one sheet needs to be replaced (such as due to soiling), it can be removed without a new sheet having to be applied. Further, the layer can be removed without, for example, moving an elderly patient or a baby off of the surface of the bed. In a preferred embodiment the soiled or top sheet can be peeled away from the remainder of the sheetset.

The sheets can be sized for use on a porta-crib, crib, twin, double, queen, king, California king, hospital bed size or even dog bed sized/shaped. Similarly the sheetset can be other bedding, such as mattress covers, pillowcases, blanket covers and the like. The fabric may be dyed any color and can be printed with any logo, such as a sports team, college name or even dates for reminders when to change the sheets (e.g. October 1, October 15, November 1) as well as with patterns and designs.

An advantage of the peelable, multi-layered, waterproof function of the product is when the top layer becomes wet or soiled, is it can be easily removed, and disposed of, so that a fresh layer can be used by the consumer.

In a preferred embodiment, the present invention is directed to a sheetset, where each sheet in the sheetset has a "comfort" side comprising a non-irritating surface, and an opposing waterproof side for serving the additional purpose of a mattress protector. In the event the sheet is soiled (such as due to incontinence) the upper (or exposed) sheet of the plurality of sheets can be removed readily and the mattress remains protected and need not be cleaned off. For an apron or bib, the waterproof side may be either the comfort side or, preferably, the exposed side.

According to an aspect of the present invention, a layered mattress protector and sheet is provided, comprising a bottom layer including a fitted portion; a plurality of layers attached to said bottom layer, each of said attached layers having a top side and a bottom side and a waterproof coating on the bottom side of each; wherein the plurality of layers are preferably collectively stitched along both of the long edges to the bottom layer; and wherein each of the layers in the plurality of layers has at least one perforation located proximal to the stitching. In other embodiments, the stitching may not be included. In yet other embodiments, there may be no perforations other than those caused by the stitching. In still other embodiments, each of said plurality of layers may have perforations and include extensions such that each could wrap around the mattress corners and themselves serve as fitted sheets.

According to another aspect of the present invention, a method of manufacturing a layered mattress protector and sheet is provided.

In one embodiment, each of the plurality of sheets could including an unperforated tab to facilitate removal of each sheet; and wherein the plurality of sheet are in a stacked arrangement such that each of the sheet has a greater (or lesser) area than a sheet located immediately below, or be equal in size.

These and other features, aspects and advantages of the present invention will become better understood with reference to the following description and claims.

DETAILED DESCRIPTION OF THE PRESENT INVENTION

Figure 1:
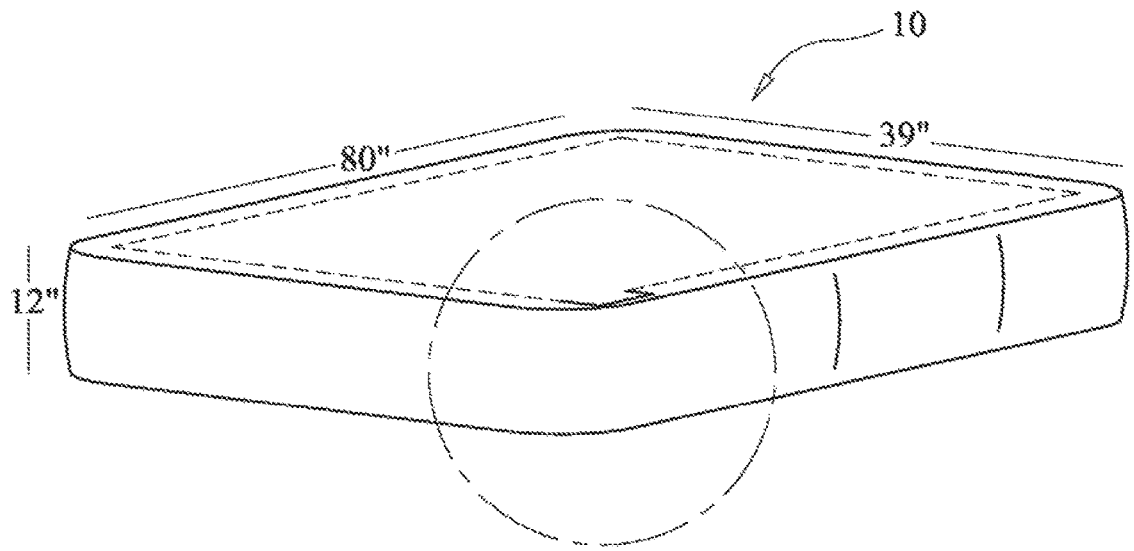
FIG. 1 depicts a layered mattress protector according to the present invention.
Figure 2:
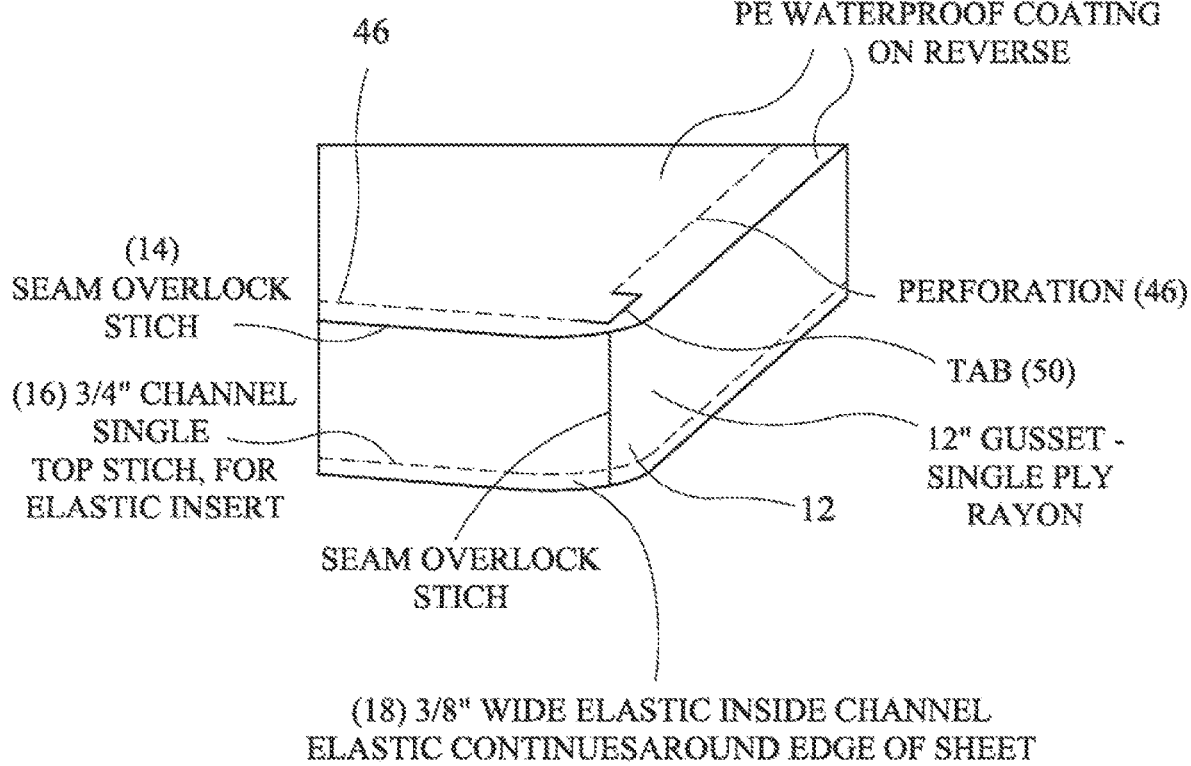
FIG. 2 depicts a layered mattress protector according to the present invention.

The present invention is directed to a multi-layered sheetset product with a plurality of removable, peelable layers sized for use as bedding with beds sized such as but not limited to porta crib, crib, changing table, toddler bed, twin-size bed, twinXL-size bed, full-size bed, queen-size bed, king-size bed, or California King-sized bed. Alternatively, the multi-layer product of the present invention is usable as bedding, an apron, a bib, etc. In another embodiment, the present invention is directed to a multi-layered mattress protector with removable, peelable or removable layers in the same size. In another embodiment, the present invention is directed to a multi-layered car seat cover with removable layers. In another embodiment, the present invention is directed to a multi-layered baby bib with removable, peelable layers. In another embodiment, the present invention is directed to a multi-layered cooking apron with removable, peelable layers.

In general, the present invention is directed to a multi-layer product, where each layer has a top side comprising a material, materials, and/or a surface pleasing to the intended use—e.g., cotton or flannel for use as a bed sheet—and an opposing side comprising a material, materials, and/or a surface conformant to other possible uses—e.g., waterproof materials for protecting a mattress or item of clothing. In addition, each layer in the multi-layer product is similarly constructed and the exposed or outer layer can easily be removed, for example, once its useful life has completed.

In general, the multi-layer product of the present invention is comprised of a plurality of layers, including a base layer and a plurality of upper layers, in which each of the plurality of upper layers may be removable one at a time.

In general, the base layer is a part of a larger assembly. For example, the base layer of an apron may include elements for attaching to a person. In another example, the base layer of a sheet or mattress cover may include the fitting sections for surrounding and attaching to a mattress as a fitted sheet would. In another example involving a sheet, the base layer may include or be attached to bed decorative borders.

In general, the product of the present invention includes a plurality of upper layers which are collectively attached to the base layer in some way such that each of said upper layers can be individually removed for discarding. Each layer can be attached using breakaway stitching or include perforations for tearing, or some combination. Typically, the aforementioned stitching or perforations might be included on less than all edges.

In any of the aforementioned embodiments, the product is preferably formed of non-woven (spunlace) fabric that preferably has a parallel or cross grain pattern with a minimum density of 20 grams per square meter. In another embodiment, the product is formed of woven fabric. In another embodiment, the product can be formed of a combination of non-woven and woven fabrics. The material used can be comprised of one of or a blend of cotton, bamboo, polyester, rayon, lyocell, hemp, flax or any other fiber that can be made into a non-woven or woven material.

Preferably the fabric of the present invention has a waterproof membrane, preferably laminated, with a minimum thickness of 0.001 mm that is either breathable (microporous) or non-breathable, on at least a portion of one side. The laminated membrane is on the bottom side of the fabric. In the preferred embodiment, the membrane is affixed to the fabric by either heat or a gluing process, and is made from at least one of polyethylene, polyurethane, poly vinyl chloride, polybutylene, latex, silicone or any other waterproofed material, either alone by itself or in combination with any other named or inferred material that is assembled into a multi-layered finished product. In a sheetset, the waterproof layer would be the layer facing the mattress and is referred to herein as the "under" side. The laminated member of the present invention might extend to the entirety of a sheet or might just extend to a portion of the sheet, depending upon need, cost, and manufacturability. For example, a sheet in the plurality of sheets might have edge stitching for connecting to a base sheet, and the laminate member could potentially only extend to the stitching.

The other side, or "over" side, is formed of materials appropriate to use, such as cotton or flannel for a bedsheet.

Particularly when used as bedding, the article of the present invention includes sheets with two sides. The side closest to the mattress is intended to provide for a water barrier so as to protect the mattress from spills, soiling, and the like. That same side also has the added feature of comparatively high friction in that it is intended not to slip or shift relative to the mattress. The other side, or the side away from the mattress and the side which will come in contact with a person, is intended to be formed of a material to provide comfort to the person. Non-limiting examples are cotton and cotton flannel. The two sides of each sheet are bonded together to form a single sheet, where the bonding is preferably through heat or gluing. However, the bonding is intended not to adversely impact the benefits described above.

In the preferred embodiment, the product is multi-layer, and each layer is individually peelable. The layers are combined together either by stitching with needle and thread, or such as by using a hook and loop system, such as Velcro®, a zipper, and/or a removable adhesive, either alone or in combination. The layers can be married to a bed skirt, or to a solid fabric, that can be made of any material, that can have elastic attached to allow for a form fit or an edge made of any material to complete the sheet, apron, baby bib or any other desired item, such as but not limited to one directed to protecting a surface.

With regard to the peel away attributes of the present invention, the goal is for a user, with limited effort, to separate the exposed sheet from the remaining sheets. To accomplish this goal, each success sheet is attached to the remainder of the sheetset in such a way so that the sheet remains functional (if, for example, used as a sheet, it should be comfortable to sleep on), yet is easily removable.

The attachment may be by means of adherence (such as by gluing or heating) or stitching, as examples. Known alternatives may alternatively be used. In an alternate embodiment, the attachment may be by stitching. Stitching may be accomplished on a sheet by sheet basis or collectively with one stitching.

In at least some embodiments, the stitching may be used in combination with perforations. For a user to remove each sheet the sheet will tear off at the perforation. In at least some embodiments, one or more tabs can be included on each sheet to facilitate removal.

In an alternative embodiment, the stitching and the material together are of the form of "breakaway" stitching, wherein a layer can be removed by a user when pulling at the location of the stitching, and the layer is torn away from the remainder of the article.

In the preferred embodiment with perforations, the perforations will extend on two opposing sides only. That is, for a bedsheet, the perforations would typically be on the two long sides of the bed. The perforations could be located along a line denoting the edge between the top and the side of the mattress, it could be along the line denoting the edge between the bottom and the side of the mattress, or it could be elsewhere. Wherever it might be, a remnant might be left behind. For an apron, the perforation might only be on one side. Once torn away, removed layer of the present invention is discardable.

In at least some embodiments, the removable layers are sized identically to one another and to the base layer. In other embodiments, the size of the removable layers may vary (becoming either smaller or larger as they become more proximal to the base layer). In some embodiments, the removable layers are generally sized for only the top of the mattress, whereas the base layer is sized comparably to a fitted sheet.

The figures included herein are directed to only some of the embodiments described herein.

The following detailed description is of the best currently contemplated modes of carrying out the invention. The description is not to be taken in a limiting sense, but is made merely for the purpose of illustrating the general principles of the invention, since the scope of the invention is best defined by the appended claims. When dimensions are included, the reader should view these as exemplary only and not limiting in any way.

Figure 6:
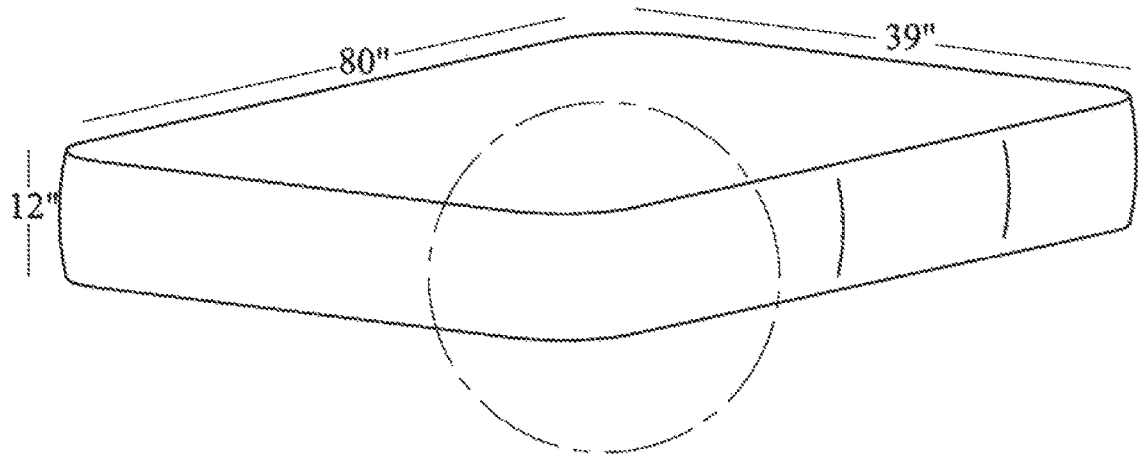
FIG. 6 depicts a layered mattress protector according to the present invention.
Figure 7:
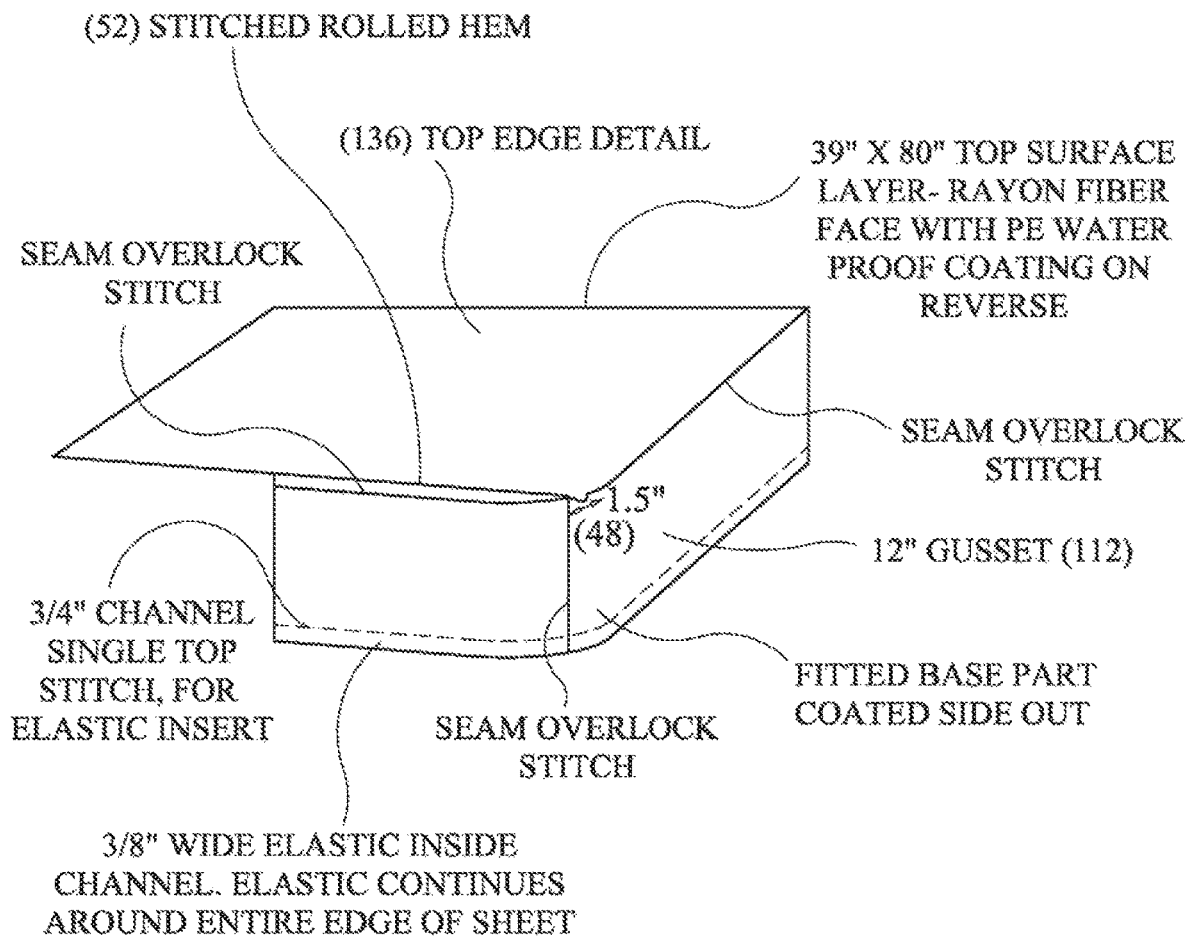
FIG. 7 depicts a layered mattress protector according to the present invention.
Figure 8:
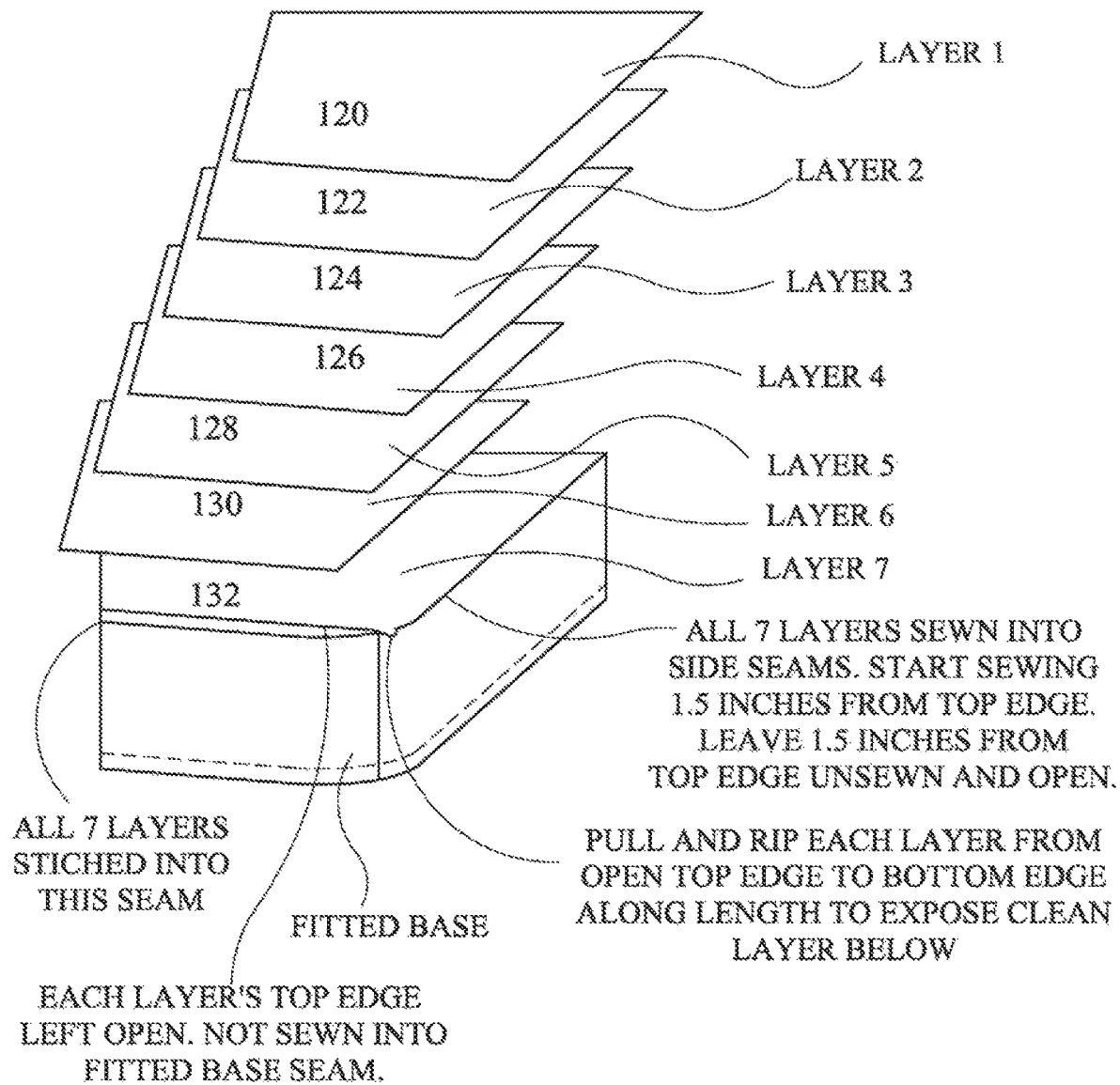
FIG. 8 depicts a layered mattress protector according to the present invention.
Figure 9:
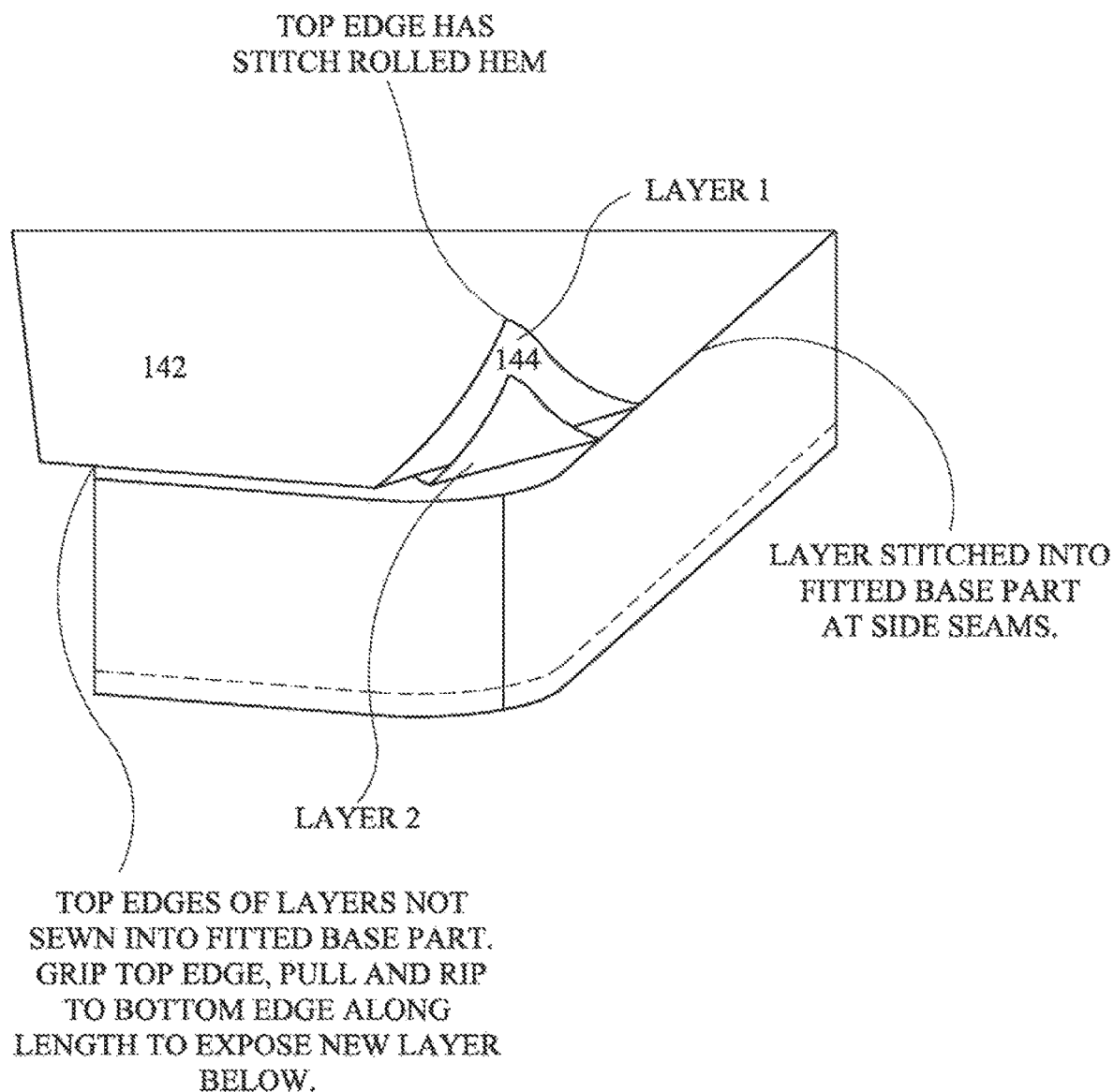
FIG. 9 depicts a layered mattress protector according to the present invention.

With reference to FIGS. 1-12, the present invention provides a layered mattress protector and sheet (10). It is noted that two embodiments are shown. FIGS. 1-5 depict one embodiment having a perforation that runs substantially parallel to the top side (34), bottom side (36), right side (40) and left side (38) and includes a tab (50). FIGS. 6-8 depict a preferred embodiment, in which there are only two perforations, that are perforation seams (80), that are substantially parallel to the right side and left side in each of at least three fitted sheet layers. They are also slightly inside the right side and left side of each of the at least three fitted sheet layers, which is to say they are located closer to the center point of each of the at least three fitted sheet layers. The layered mattress protector and sheet may have a bottom fitted portion (12, 112); at least three fitted sheet layers (e.g. 20, 22, 24, 26, 28, 30, 32, 120, 122, 124, 126, 128, 130 and 132). While there may be any number of fitted sheet layers, according to one preferred embodiment there are seven layers. Each fitted sheet layer has a top side (34, 134), bottom side (36, 136), right side (40, 140) and left side (38, 138) and an upper portion (42, 142) and lower portion (44, 144). Note that the numbers for the different sides are shown for one layer of the many layers of the fitted sheet layers. Each layer would have the same sides. There may be a waterproof polyethylene coating on the lower portion (44, 144) of each of the at least three fitted sheet layers. It should be understood that a waterproof layer would be equivalent to a waterproof coating and the terms are interchangeable. The upper portion of each fitted sheet layer may be rayon (also referred to as spunlace rayon). Then at least three fitted sheet layers are stitched along the right side (40, 140) and left side (38, 138) to the bottom fitted portion (12, 112) and the top side (34, 134) and bottom side (36, 136) are unstitched. Each of the at least three fitted sheet layers has at least one perforation (46, 146). According to one embodiment, depicted in FIGS. 1-5, there is a single perforation that runs substantially parallel to the top side (34), bottom side (36), right side (40) and left side (38) and includes a tab cutout portion (50). The term perforation may be a series of small holes that allows for the fitted sheet layers to be removably attached, it may also be a perforation seam, that is a seam that is stitched creating holes, or perforations, yet having the added stability of a seam. The perforation (46, 146 also referred to as a perforation seam) creates a portion of the fitted sheet layer that is smaller than the entire fitted sheet layer that may be easily removed to reveal another, new fitted sheet layer below it. There is also a waterproof coating on the lower portion (44, 144) of each of the at least three fitted sheet layers. The at least three fitted sheet layers are stitched along the right side (40, 140) and left side (38, 138) to the bottom fitted portion (12, 112) and the top side (34, 134) and bottom side (36, 136) are unstitched. Each of the at least three fitted sheet layers has at least one perforation (46, 146) that is at least substantially parallel to the right side and left side in each of at least three fitted sheet layers.

The at least three fitted sheet layers may be stitched along the right side (40, 140) and left side (38, 138) to the bottom fitted portion (12, 112) along a portion of the right side (40, 140) and a portion of the left side (38, 138) to leave an unstitched portion (48) along a portion of each end of the right side and the left side. The unstitched portion (48) along a portion of each end of the right side and the left side may be between one and three inches, preferably one and a half inches. This allows for the easy removal of each layers of the at least three fitted sheet layers. It is not required that the unstitched portion (48) be along both sides, it may be along either a portion of the right side (40, 140) or a portion of the left side (38, 138). It should be towards one end of the right (right side (40, 140) or the left side (38, 138). The term end is intended to denote the area close to the top side (34, 134) or the bottom side (36, 136). The unstitched portion (48) along a portion of at least one end of the right side and the left side may be between one and three inches, preferably one and a half inches.

Figure 3:
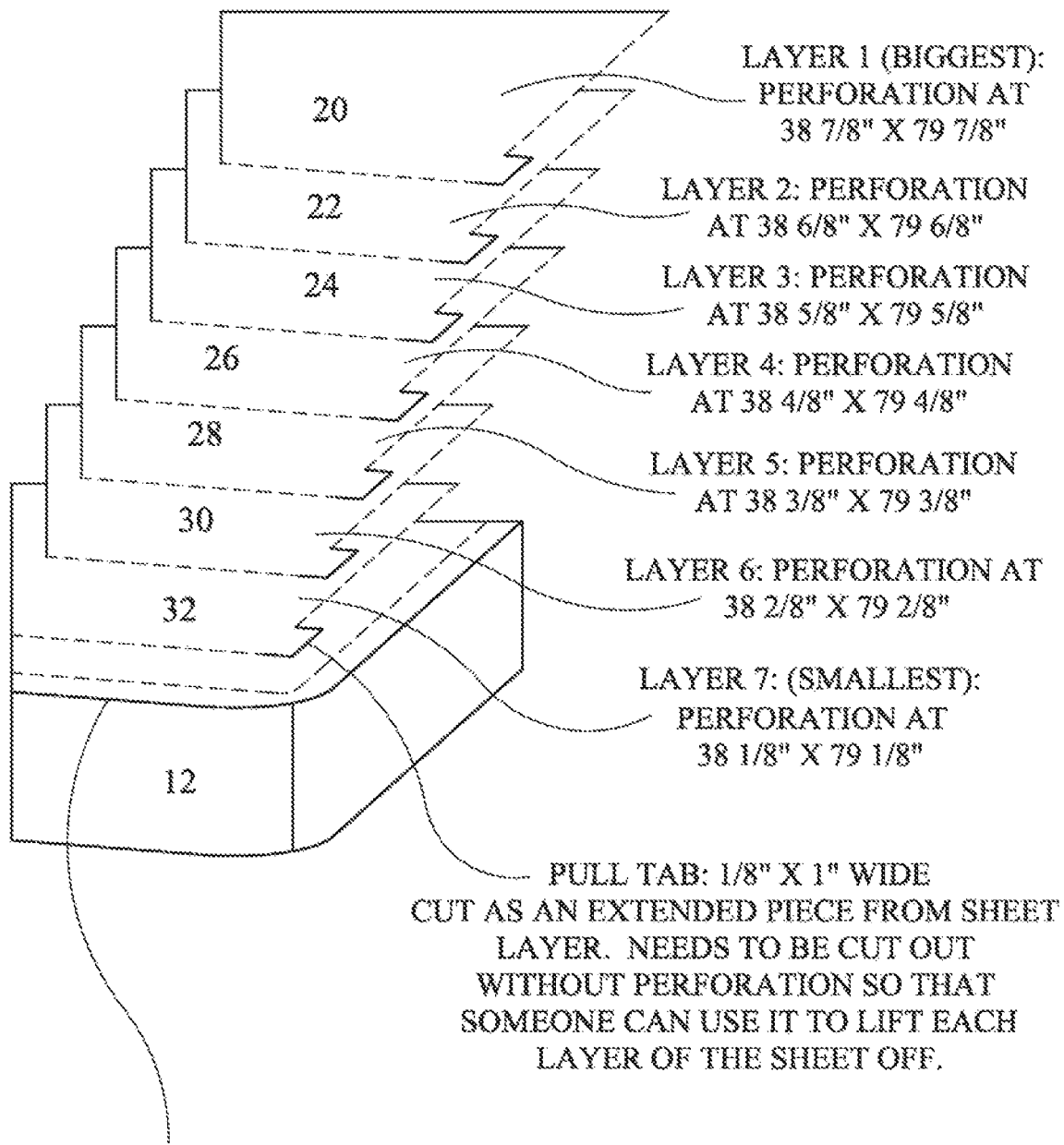
FIG. 3 depicts a layered mattress protector according to the present invention.
Figure 4:
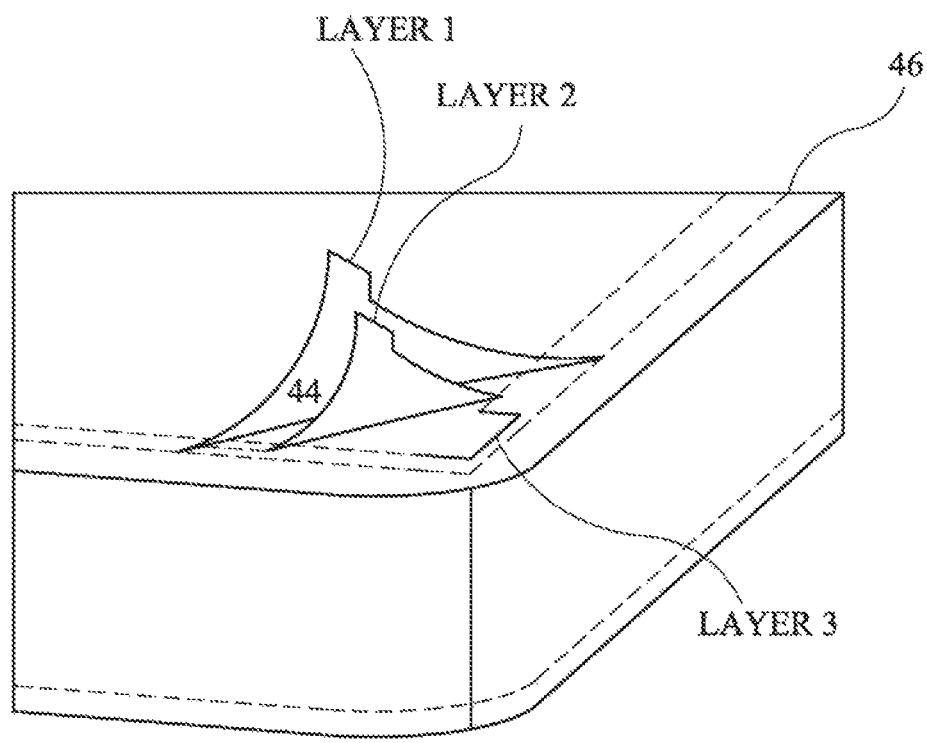
FIG. 4 depicts a layered mattress protector according to the present invention.
Figure 5:
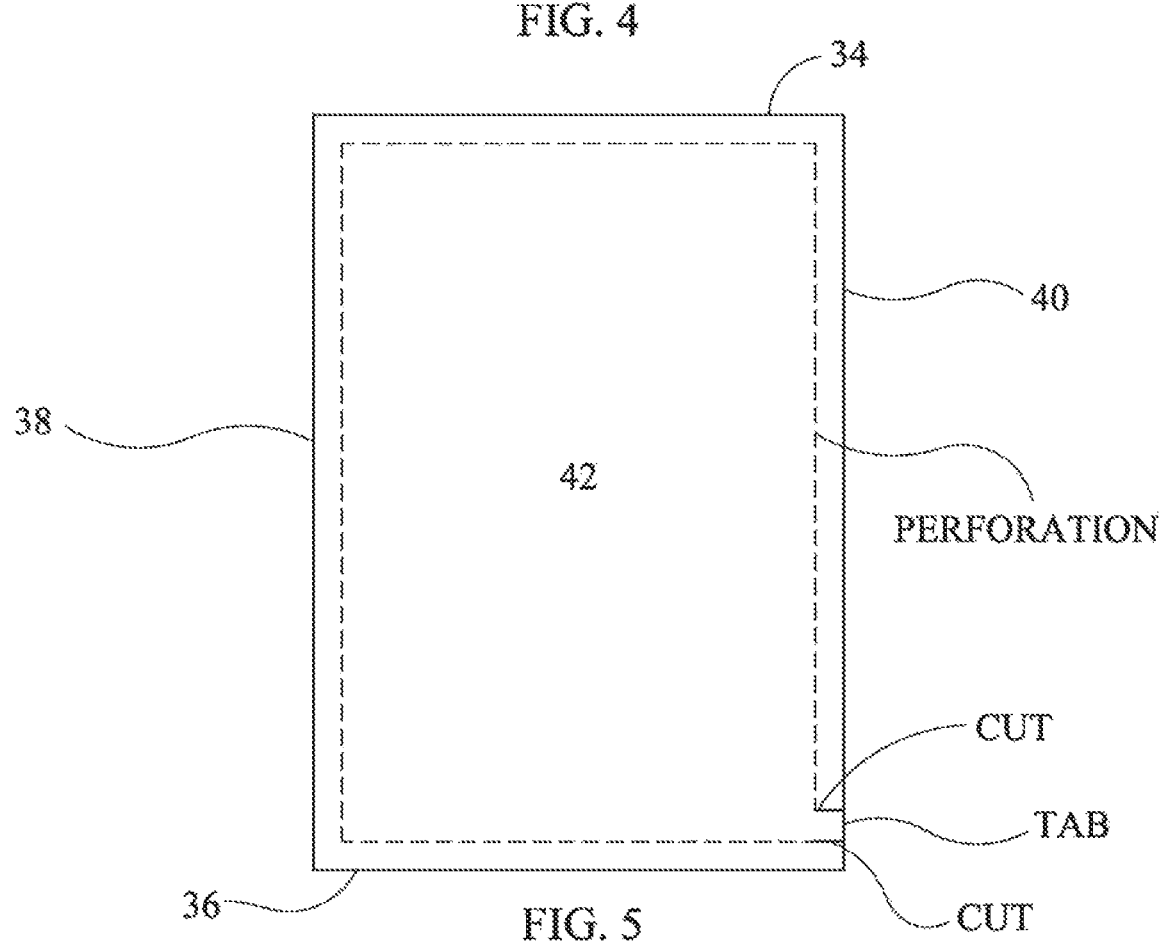
FIG. 5 depicts a layered mattress protector according to the present invention.

The upper portion (42) of each fitted sheet layer may any fabric that is desirable to the user, such as polyester and/or rayon fiber. The fitted sheet layers may be all the same size. According to an alternate embodiment, each of the at least three fitted sheet layers is slightly larger than the layer that is below it. As shown in FIG. 3, fitter sheet layer (20) is the biggest and has a perforation at 38⅞×29⅞, fitted sheet layer (22) is slightly smaller and has a perforation at 38⁶⁄₈×29⁶⁄₈, fitted sheet layer (24) is slightly smaller and has a perforation at 38⅝×29⅝, fitted sheet layer (26) is slightly smaller and has a perforation at 38⁴⁄₈×29⁴⁄₈, fitted sheet layer (28) is slightly smaller and has a perforation at 38⅜×29⅜, fitted sheet layer (30) is slightly smaller and has a perforation at 38²⁄₈×29²⁄₈ and fitted sheet layer (32) is slightly smaller and has a perforation at 38⅛×29⅛. As can be seen each perforated portion of the at least three fitted sheet layers is slightly larger than the layer that is below it.

Each perforated portion, according to an alternate embodiment, may have a tab cutout portion (50). The tab cutout portion (50) may be between a portion of the perforated portion (46) and at least one of the top side (34), bottom side (36), right side (40) and left side (38) of the at least three fitted sheet layers. According to one embodiment, the tab cutout portion (50) is away from the top side (34). This is to prevent inadvertent removal of a layer and any possible discomfort to the user. The top side (34) may be sewn with a rounded stich that edges the top side to provide an edged top side. The top side (34) may also be stitched to provide a stitched rolled hem top side (54). There may also be a printed item (56) on the upper portion of the at least three fitted sheet layers. The printed item (56) may be a school logo, or it may be, by way of example, say "October" as a reminder to pull off the layer at the end of October. Of course, it could say October 1, the next layer October 15, the next layer November 1, etc. In this way, the user is reminded of when to change their sheets.

Another aspect of the present invention provides a method of method of manufacturing a layered mattress protector and sheet, comprising: providing a bottom fitted portion (12, 112); providing at least three fitted sheet layers (e.g. 20, 22, 24, 26, 28, 30, 32, 120, 122, 124, 126, 128, 130 and 132), each fitted sheet layer having a top side (34, 134), bottom side (36, 136), right side (40, 140) and left side (38, 138) and an upper portion (42, 142) and lower portion (44, 144), wherein the lower portion (44, 144) of each of the at least three fitted sheet layers has a waterproof coating; providing at least one perforation (46, 146) that is at least substantially parallel to the right side and left side in each of at least three fitted sheet layers; stitching the at least three fitted sheet layers along the right side and left side to the bottom fitted portion and leaving the top side and bottom side unstitched. The step of stitching the at least three fitted sheet layers along the right side (40, 140) and left side (38, 138) to the bottom fitted portion (12, 112) and leaving the top side (34, 134) and bottom side (36, 136) unstitched may be further comprising the step of: stitching along the right side and left side to the bottom fitted portion to leave an unstitched portion (48) along at least one end of the right side and the left side. The unstitched portion (48) along at least one end of the right side and the left side is between one and three inches, preferably one and a half inches. Each of the at least one perforations (46, 146) of the at least three fitted sheet layers may be slightly larger than the layer that is below it. There may be the step of providing a tab cutout portion (50). The tab cutout portion (50) may be along at least one of the top side, bottom side, right side and left side of the at least three fitted sheet layers. There may be the step of sewing the top side with a rounded stich that edges the top side to provide an edged top side. There may be the step of stitching the top side to provide a stitched rolled hem top side. There may also be the step of printing a printed item (56) on the upper portion of each of the at least three fitted sheet layers.

Figure 10:
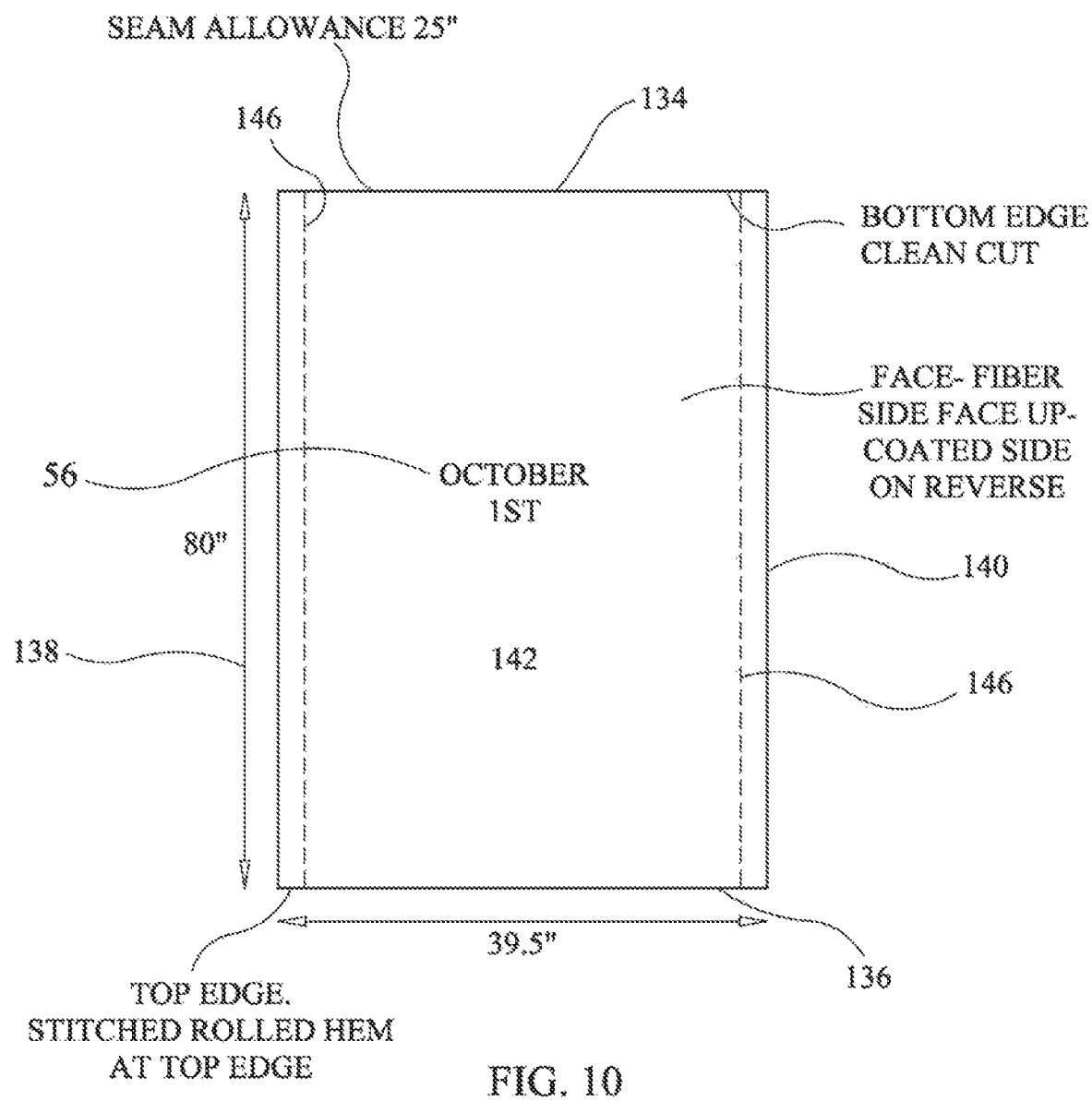
FIG. 10 depicts a layered mattress protector according to the present invention.
Figure 11:
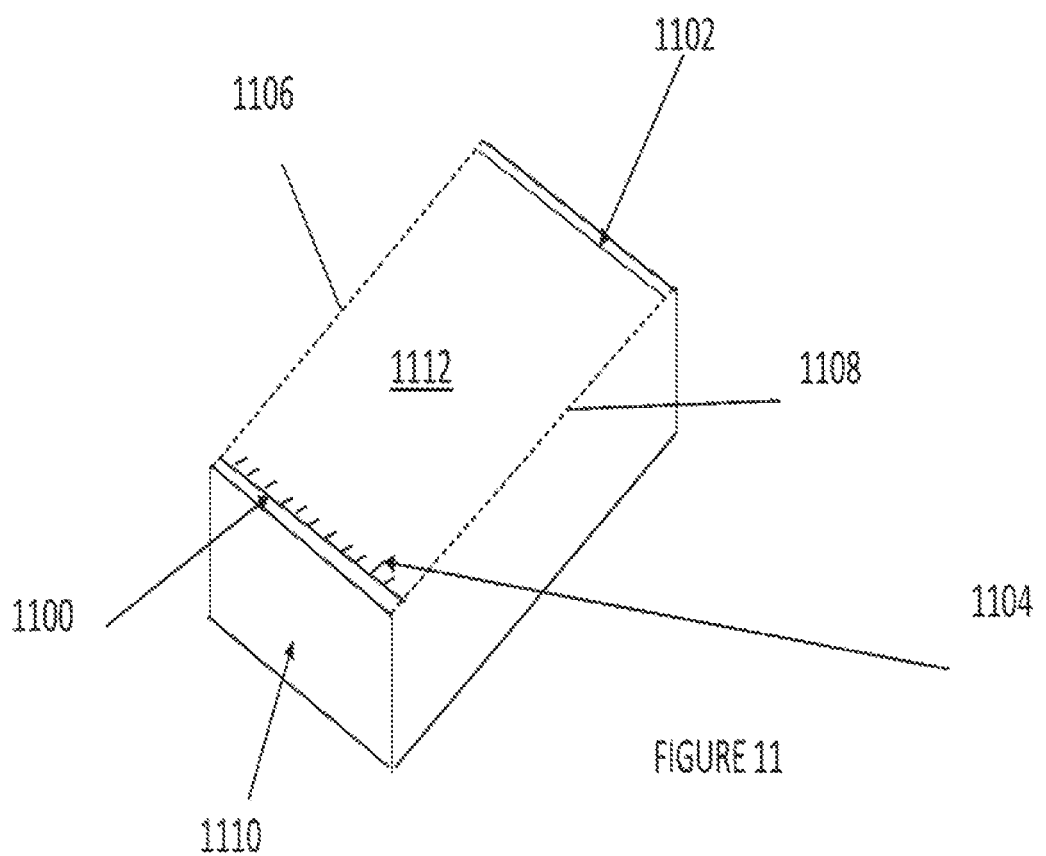
FIG. 11 depicts a layered mattress protector according to the present invention.
Figure 12:
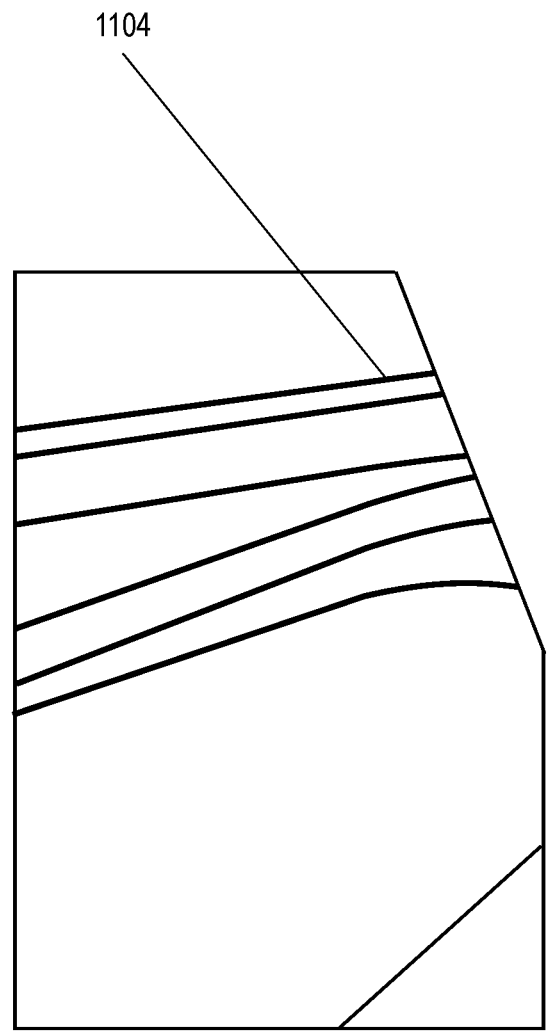
FIG. 12 depicts a layered mattress protector according to the present invention.

FIGS. 10, 11 and 12 depict a layered mattress protector according to the present invention.

FIG. 11 depicts a preferred embodiment of the present invention. A layered mattress protector and sheet is provided with a bottom fitted portion (III 0); at least three fitted sheet layers (1112), each fitted sheet layer having a top side (1100), bottom side (1102), right side (1108) and left side (1106) and an upper portion (1112) and lower portion (not seen in FIG. 11, would be the portion opposing the upper portion (1112) on the underneath of the three fitted sheet layers). Also note that the at least three fitted sheet layers are layered, so FIG. 11 only depicts one of the layers, but there are at least three fitted sheet layers, as depicted in other figures. There is a waterproof coating on the lower portion of each of the at least three fitted sheet layers (1112). The at least three fitted sheet layers (1112) are stitched along the right side (1106) and left side (1108) to the bottom fitted portion (1110) the stitch creating at least one perforation seam and the top side (1100) and bottom side (1102) are unstitched to the bottom fitted portion (1110) leaving open ends; and the top side (1100) is an edged top side (1104). FIG. 12 depicts a picture of the edged top side of each of the at least three fitted sheet layers (1112) according to the present invention and the top side being unstitched. It should be understood that the foregoing relates to preferred embodiments of the invention and that modifications may be made without departing from the spirit and scope of the invention as set forth in the following claims.

The invention claimed is:

1. A multi-layered protector article, consisting of:
a generally rectangular unfolded base layer; and
a generally rectangular upper portion consisting of a plurality of removable layers overlaid on one another, each removable layer consisting of a waterproof membrane on a first side and an unperforated tab, said upper portion commonly stitched to and with said base layer with stitching, said stitching consisting of thread or string, at least some of said stitching co-located with a plurality of perforations where at least some of said stitching is used to demarcate the perforations;
wherein each of said plurality of removable layers is defined by said plurality of perforations along at least one side and each said removable layer is individually removable from said article at said perforations.

2. The multi-layered article of claim 1, wherein said generally rectangular base layer further includes a portion arranged to wrap around the side of a mattress and elasticized edging for fitting to said mattress with each said waterproof layer functioning as a mattress protector.

3. The multi-layered article of claim 1, wherein said article is a clothing protector.

4. The multi-layered article of claim 1, wherein said article is a seat cover.

5. The multi-layered article of claim 1, wherein said stitching is a hook and loop stitching.

6. The multi-layered article of claim 1, wherein said stitching is limited to being along one edge of said upper portion.

7. The multi-layered article of claim 1, wherein the side opposing the side with said waterproof membrane is comprised of at least one of cotton, rayon, polyester, bamboo, lyocell, hemp, or flax.

8. The multi-layered article of claim 1 wherein said membrane is micro-porous or non-porous and has a thickness of at least 0.001 mm.

9. The multi-layered article of claim 1, wherein said membrane is affixed to a removable layer using heat or a gluing process.

10. The multi-layered article of claim 1, wherein each layer of said plurality of removable layers is removable through use of said perforations and tab.

11. The multi-layered article of claim 1, wherein said article is formed, at least in part, of a non-woven material with a parallel or cross grain pattern with at least about 20 grams per square inch.

12. The multi-layered article of claim 1, wherein the waterproof membrane comprises at least one of at least one of polyethylene, polyurethane, polyvinylchloride, polybutylene, latex, or silicone.

13. The multi-layered article of claim 1, wherein said stitching is break away stitching.

14. The multi-layer article of claim 2 wherein the stitching co-located with a plurality of perforations is proximal to the elasticized edge.

15. The multi-layer article of claim 2, wherein said stitching is located on the article in the portion lying flat over a mattress.

16. The multi-layer article of claim 1, wherein a second side of each removable layer faces away from said base layer, and is formed of a at least of non-woven fabric.

17. The multi-layer article of claim 1, wherein said base layer includes an element for attaching to a person.

18. The multi-layer article of claim 1, wherein said waterproof membrane includes a laminated side.

19. The multi-layer article of claim 1, wherein upon removal of a layer, a remnant of said layer is left behind.

20. The multi-layer article of claim 1, wherein said perforations are arranged at least in part linearly.

* * * * *